US006977171B1

(12) United States Patent
Dennis et al.

(10) Patent No.: US 6,977,171 B1
(45) Date of Patent: Dec. 20, 2005

(54) DETOXIFICATION AND DECONTAMINATION USING NANOTECHNOLOGY THERAPY

(75) Inventors: Donn M. Dennis, Gainesville, FL (US); Charles R. Martin, Gainesville, FL (US); Timothy E. Morey, Gainesville, FL (US); Richard E. Partch, Gainesville, FL (US); Dinesh O Shah, Gainesville, FL (US); Manoj Varshney, Gainesville, FL (US)

(73) Assignee: University of Florida, Gainesville, FL (US)

( * ) Notice: Subject to any disclaimer, the term of this patent is extended or adjusted under 35 U.S.C. 154(b) by 415 days.

(21) Appl. No.: 09/978,344

(22) Filed: Oct. 16, 2001

Related U.S. Application Data

(60) Provisional application No. 60/281,293, filed on Apr. 3, 2001.

(51) Int. Cl.[7] .................... B09B 3/00; A61K 9/16; A01N 25/00
(52) U.S. Cl. ............ 435/262.5; 424/401; 424/484; 424/497; 514/937; 514/938; 514/939
(58) Field of Search .................. 424/401, 484, 424/497; 435/262, 262.5; 514/937, 938, 514/939

(56) References Cited

U.S. PATENT DOCUMENTS

| | | | |
|---|---|---|---|
| 5,449,613 A | 9/1995 | Dordick et al. | |
| 5,667,764 A | 9/1997 | Kopia et al. | |
| 5,695,775 A | 12/1997 | van Blucher et al. | |
| 5,914,436 A | 6/1999 | Klabunde | |
| 5,990,373 A | 11/1999 | Klabunde | |
| 5,993,831 A | 11/1999 | Ribier | |
| 6,057,488 A | 5/2000 | Koper | |
| 6,395,299 B1 * | 5/2002 | Babich et al. | .............. 424/484 |

FOREIGN PATENT DOCUMENTS

| | | |
|---|---|---|
| WO | WO 00/4736 A1 | 1/2000 |
| WO | WO 00/47236 A1 | 8/2000 |
| WO | WO 01/17648 A1 | 3/2001 |

OTHER PUBLICATIONS

Koper et al., *Development of Reactive Topical Skin Protectants against Sulfur Mustard and Nerve Agents*, J Appl. Toxicol. 19, S59-S70 (1999).

Gill and Ballesteros, Degradation of Organophosphorous Nerve Agents by Enzyme-Polymer Nanocomposites: Efficient Biocatalytic Materials for Personal Protection and Large-Scale Detoxification, Biotechnology and Bioengineering vol. 70, No. 4, pp 400-410 (2000).

International Search Report for PCT/US02/06114.

\* cited by examiner

*Primary Examiner*—Ralph Gitomer
*Assistant Examiner*—Kailash C. Srivastava
(74) *Attorney, Agent, or Firm*—Brinks Hofer Gilson & Lione

(57) ABSTRACT

A particle with two regions, the first region contains a detoxifying enzyme and a second region that partitions toxic compounds. The particle may be a nanoparticle.

11 Claims, 9 Drawing Sheets

Figure 2:
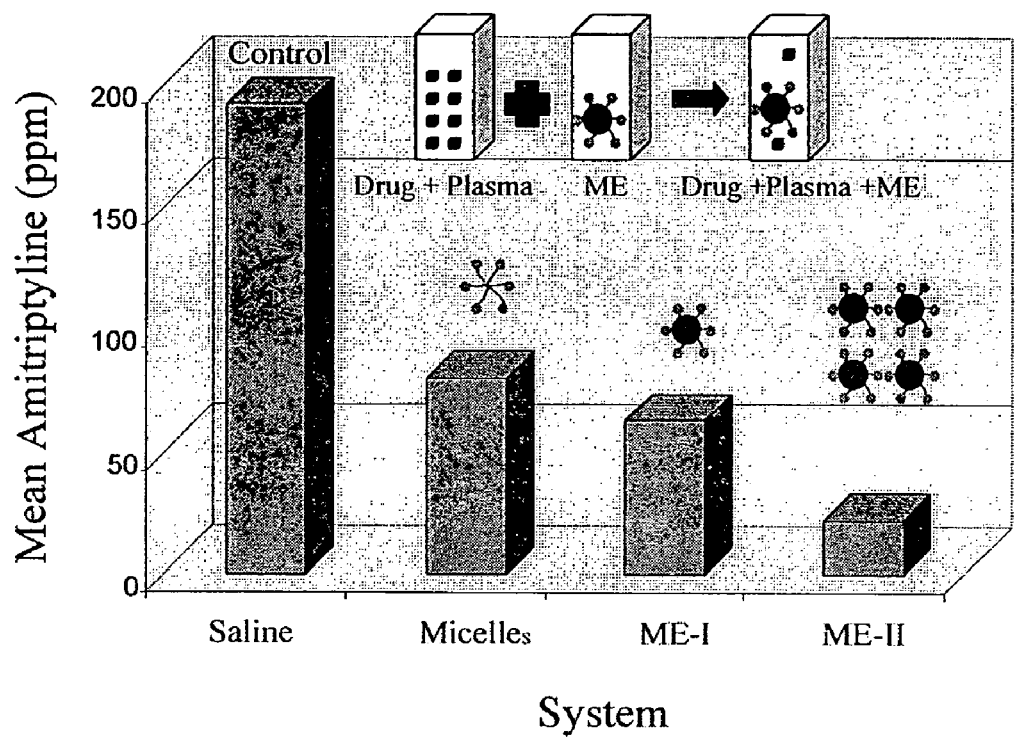

| Functionalized Particulate Systems | Features |
|---|---|
| Soft Particles (microemulsions) | • Nanoscale oil core<br>• Fluid surface film |
| Soft/Hard Particles (Core-Shell/Porous/ Gels/Nanotubes) | • Hydrophobic core<br>• Porosity allows drug penetration |
| Templated Particles (Porous/Gels/Nanotubes) | • Hard surfaces activated for specific adsorption of toxin |
| P450 Enhanced Nanoparticulates | • Enzyme in oil core or bound to hard surfaces degrades toxin |

FIGURE 1.

Scanning Electron Micrographs of a Microporous Alumina Template Membrane Prepared in the Martin Lab
Surface Image     Cross- Section Image
3A. 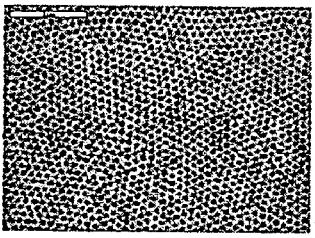  3B.
Very high density of monodisperse pores (dia.= 60nm).
Pore diameter can be controlled at will.
Scanning Electron Micrograph of the Surface of the Alumina Template Membrane Used
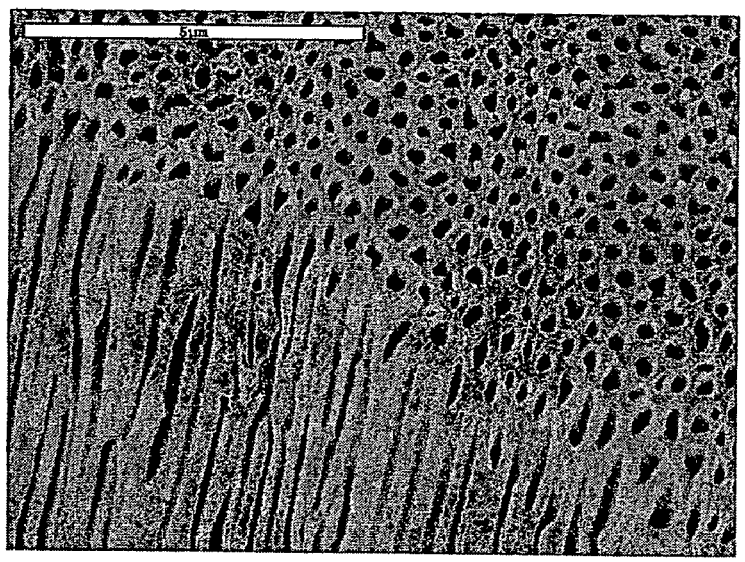
3C.
FIGURE 3.

DETOXIFICATION AND DECONTAMINATION USING NANOTECHNOLOGY THERAPY

RELATED APPLICATIONS

This application claims priority to U.S. Provisional Application Ser. No. 60/281,293, filed Apr. 3, 2001.

STATEMENT OF GOVERNMENTAL INTEREST

The subject matter of this application has been supported by a research grants from the National Institutes of Health (N1H) (Grant No. DK4902989) and the Office of Naval Research (Grant No. N000-14-00-1-0-180). The government may have certain rights in this invention.

BACKGROUND OF THE INVENTION

Drug toxicity in humans can result from causes such as therapeutic misadventure, illicit drug ingestion, or suicide attempt. Drug toxicity is a major health care problem throughout the world and results in significant financial costs as well as potential harm including possible death. Unfortunately, the vast majority of life-threatening drug intoxications do not have specific pharmacological antidotes to ameliorate their physiological effects. Other than providing supportive therapy to affected individuals, often little can be done to help individuals affected by most drug intoxications. Drug toxicity can also be a problem in veterinary medicine.

When a chemical, such as xenobiotic, is administered to an organism, two events must generally occur for a biological response to be triggered. First, the xenobiotic must be transported to the site of action (the "target site"). Second, after arriving at the target site, the xenobiotic must interact with the intended target in an appropriate manner. Interaction of a xenobiotic with the target site is governed largely by two factors:

a. the size and shape of the xenobiotic which controls how well the xenobiotic interacts with the target site; and b. the nature and relative positions of appropriate functional groups of the xenobiotic which affects the type and strength of its interaction with complementary groups of the receptor.

Many physicochemical properties can be used to model receptor interaction. For example, molar volume (MV) is an overall measure of molecular size, while the energy of the lowest unoccupied molecular orbital ($E_{LUMO}$) is a crude measure of the electron-accepting ability of a given chemical compound. Several methods for treating various drug intoxications currently exist. Immunotoxicotherapy can produce purified drug-specific antibodies to treat some potentially fatal cases of drug poisoning. By linking the toxic drug to albumin and using it as a hapten, high affinity antibodies with excellent specificity can be theoretically formed for use against a particular molecule or a class of molecules. The last several years have brought major innovations in the safety and efficacy of immunotoxicotherapy. In addition, advances have occurred in the processes of fragmentation which permits a greater volume of distribution (VOD) and diminished risk of sensitization and enhanced renal elimination.

Volume of distribution is defined as the volume of fluid that would be necessary to contain the amount of drug in the body at a uniform concentration equal to that in plasma. Thus, the definition assumes the body is a single homogeneous fluid compartment and the drug is evenly distributed throughout. The VOD may exceed the actual volume of the body. In application, VOD defines the concentration following one intravenous dose and roughly describes tissue penetration. A large VOD indicates good tissue penetration, while a small VOD indicates poor tissue penetration.

The binding portion of the antibody, known as the Fab fragment, has been found to reduce the physiological effects of drugs, such as digoxin, PCP, cocaine, colchicine, and tricyclic antidepressants in various animal models. However, despite these reported advances and the purported potential advantages of antibody use over other drug intoxication therapies, only one commercial antibody product is currently available to treat drug overdoses in humans. Digibind®, a digoxin immune Fab, is a lyophilized powder of antigen binding fragments (Fab) derived from specific antibodies raised from sheep. It has been shown to be highly effective in treating the life threatening cardiotoxic effects of digoxin, an inhibitor of the myocardial $Na^+/H^+$ ATPase pump.

A number of reasons explain the lack of widespread immunotoxicotherapy use in humans. First, there is no guarantee that a specific antibody can be produced that can effectively bind to a given target toxic drug molecule or its associated class of molecules. In addition, since antibodies are directed at specific chemical moieties, antibodies cannot offer broad substrate detoxification to an entire class of intoxicants.

Moreover, the ability and capacity of antibodies to effectively bind drug toxins is severely limited by each antibody's stoichiometry. One Fab fragment can typically bind only one target molecule. This property limits the binding effectiveness of these antibodies, especially for drug toxicities that typically include large doses and extensive tissue and plasma protein binding (e.g., amiodarone).

Immunotoxicotherapy has also been shown to be only effective in situations where the amount of toxic drug in the bloodstream is relatively small and protein and tissue binding is not significant. An example of a drug suitable for immunotoxicotherapy is the drug digoxin. The plasma concentration of digoxin that begins to cause cardiac toxicity is approximately 1.7 ng/ml, with only approximately 25±5% of it being bound in plasma. In contrast, the same toxic plasma concentrations for the drugs amiodarone and amitriptyline begin at approximately 3,500 ng/ml and 1,000 ng/ml, respectively, corresponding to 99.98±0.01% and 94.8±0.8% drug binding in plasma, respectively. This fact largely explains why antibodies are more effective against drugs such as digoxin which cause toxicity at low concentrations (approximately 1 nM).

In addition, most antibodies that have been produced have been formed for use against toxic drug molecules in humans were isolated from animals (e.g. Digibind® is produced from sheep antibodies). Therefore, there remains a potential risk of allergy and aphylactic shock, because the Fc portion of the antibody, which is the most antigenic portion of the antibody, is cleaved from the binding portion of the immunoglobulin (Fab fragment) using papain. Also, unless major advances are made in the molecular production of antibodies, particularly human monoclonal antibodies, the quantity of antibodies which can be formed is very limited. Consequently, it is extremely expensive and impractical to manufacture the large quantities of antibodies required to treat drug toxicities involving drugs that are highly protein and tissue bound as well as toxicities arising from drugs having relatively high toxic blood concentrations.

Even for a drug like digoxin that causes drug toxicity at much lower concentrations than do drugs such as amiodarone and amitriptyline and is much less protein bound, the cost of treatment can still be prohibitive. For example, depending upon the blood concentrations of digoxin, 10–20 vials or more of Digoxin immune Fab (ovine), trade named Digibind®, may be required to effectively treat a 70 kg (155 pound) individual. This can translate to a cost of approximately $10,000 to $30,000. Accordingly, the cost of using an agent such as Digibind® can be prohibitively expensive where the potency of the drug is much lower and consequently a much greater amount of toxic drug (e.g., amiodarone or amitriptyline) would be required to be bound by the antibody.

Therefore, in the current state of development, antibodies are not a viable option to treat the vast majority of drug overdoses. Furthermore, even if new advances in molecular medicine allowed human-derived antibodies to be produced in mass quantities at a reasonable cost, their slow onset time of actions in humans is another limiting factor. For example, the median time to initial response for Digibind® is reported to be 18 minutes. Only 75% of patients showed evidence of response within 60 minutes. Slow response combined with inability to provide broad substrate detoxification and high cost are expected to continue to make antibodies a poor choice for the treatment of drug toxicity.

Another method for reducing toxic drug effects is infusion of enzymes into the blood. This method may be feasible to ameliorate toxic in-vivo effects of drugs. Specifically, the acute physiological effects of cocaine in various animal species have been reported to be acutely ameliorated using animal and human butyrylcholinesterase, the principal esterase in the blood that degrades cocaine to its major metabolites.

While sometimes effective, this approach suffers from a number of drawbacks. First, water-soluble plasma enzymes, such as butyrylcholinesterase, do not metabolize the majority of drugs. Second, infusion of enzymes directly into the blood does not permit the beneficial and synergistic actions of initially partitioning the drug at high local concentrations in an environment containing high concentrations of an enzyme. The reaction velocity (V) of enzymes generally obey Michaelis-Menten kinetics. Thus, although V is proportional to the substrate concentration at low concentrations (first order) the reaction velocity is constant at higher substrate concentrations (zero order). Zero order kinetics largely negates the potential treatment advantage derived from having a high local enzyme concentration.

Although the infusion of water soluble enzymes, such as butyrylcholinesterase, into the blood can cause rapid and efficient conversion of ester-type drugs, this approach is not applicable for P450 microsomal fractions. P450 microsomal fractions require a lipid environment and are extensively integrated into the cellular membranes of hepatocytes and other cells.

Another method for detoxifying drugs is hemodialysis. Hemodialysis can be used to detoxify the blood stream from various drugs and metabolic disorders using hemoperfusion and hemodialysis. However, for a number of reasons, this method is not appropriate for the vast majority of life threatening drug overdoses.

First, many drugs that cause toxicity in humans are not susceptible to removal from the body by hemodialysis, either due to their physicochemical properties or their large volumes of distribution. For example, despite being primarily renally excreted (approximately 65% of an administered oral dose), digoxin cannot be effectively dialyzed, whereas amiodarone cannot be effectively removed from the blood due to a VOD of approximately 66 L/kg. This large VOD means that most amiodarone is sequestered in compartments other than the intravascular space. In the latter case, hemodialysis would be futile because the volume of blood required to circulate through a dialysis machine would be too large to be practical.

Second, the rate of removal of a drug from the blood must be taken into account. Hemodialysis and hemoperfusion are slow (e.g., generally hours) to generally remove drugs at toxic levels from the bloodstream.

For example, the intoxications of two testbed drugs, amiodarone and amitriptyline, are frequently life threatening because of their severe effects on cardiac function. Accordingly, treatment under these conditions must be initiated immediately or a patient may die. Consequently, hemodialysis or hemoperfusion cannot be used as a treatment for fast acting life threatening drugs such as amiodarone and amitriptyline. In addition, these approaches require the placement of large arterial and venous cannula prior to circulation of blood through the dialysis machine. As a result of its shortcomings, hemodialysis has minimal applications in treating drug toxicity. However, hemodialysis may be applicable for toxic drugs with low volumes of distribution and for those toxins that do not immediately produce life threatening effects.

Another method for treating drug poisonings is the use of specific pharmacological antidotes. However, of the many types of drug poisonings in humans, only a few have identified specific pharmacological antagonists that can be used to quickly and selectively reverse their deleterious physiological effects. Probably the best two examples of effective pharmacological antidotes are the muscarinic-cholinergic and narcotic receptor antagonists, atropine and naloxone, respectively. Atropine blocks the physiological effects of excessive acetylcholine levels on muscarinic receptors. Therefore, it is effective against organophosphate-based insecticides as well as nerve gas agents.

In an analogous manner, naloxone blocks most of the physiological effects (e.g., respiratory depression) of narcotic overdosage. Therefore, it is effective in reversing the physiological effects of potent narcotics such as heroin and fentanyl. Although receptor antagonists are highly efficacious, rapid and specific in reversing these types of life threatening drug poisonings, they do so by preventing access of the agonist to its cellular locus of action (i.e., the receptor). Receptor antagonists neither alter the free blood drug concentration, nor promote its biotransformation to less toxic metabolites and its ultimate excretion from the body. This is clinically important, because deaths have been reported when the biological effects of a receptor antagonist outlives that of the drug toxin.

In contrast to the above situations where life saving measures frequently must be instituted immediately or death may occur, a different type of pharmacological antidote, a biochemical one, may also be used to treat drug toxicity problems that are less emergent in nature. The best-known example of this type of treatment is using N-acetylcysteine to replenish hepatic stores of glutathione in the setting of acetaminophen (Tylenol®) overdosage.

However, high levels of acetaminophen in the blood deplete liver sulfhydryl stores. This, in turn, allows the formation of a highly reactive intermediate, N-acetyl-benzoquinoneimine, that can cause free radical injury to the liver. Acetaminophen toxicity is a slow ongoing process which develops over a period of several hours to days. Accordingly, it is not necessary to treat acetaminophen toxicity with a method which quickly decreases the chemical level to save lives. An effective treatment to acetaminophen overdosage is already available. By replenishing hepatic stores of glutathione using N-acetylcysteine orally or intravenously, the liver can be protected against further injury from toxic metabolites of acetaminophen. However, biochemical antidotes can only be used to treat the narrow class of drugs which result in slow acting toxicity.

Thus, based on the lack of effectiveness of currently available treatments for most drug intoxications, there is a need for new and improved technologies for rapidly and inexpensively reducing the free drug concentration for a wide variety of drugs. Drugs to be treated may be introduced in potentially toxic levels into living organisms as well as onto non-biological surfaces or bodies such as metal or wood.

SUMMARY

A method for removal of at least one target chemical from a region includes the steps of adding a nanoparticle size bioparticle to the region and partitioning at least a portion of the target chemical into or onto the bioparticle. The method results in reducing the active concentration of the target chemical. The region can be a solution. Partitioning can result from differences in physicochemical properties between the bioparticle and the target chemical and/or from adsorption of the target chemical on a surface of the bioparticle.

A method for removal of at least one target chemical from a region includes the steps of adding a nanoparticle size bioparticle having at least enzyme incorporated therein to the region and biotransforming at least a portion of the target chemical into at least one substantially inactive metabolite. The region can be a solution. The enzyme can preferably be a genetically cloned enzyme.

A method for removal of at least one target chemical from a region includes the steps of adding a bioparticle having at least one enzyme incorporated therein and partitioning at least a portion of the at least one target chemical into or onto the bioparticle. The method results in a portion of the target chemicals being transformed into at least one substantially inactive metabolite. The region can be a solution. The bioparticle can be a nanoparticle. In one embodiment, the nanoparticle can include a silica nanotube having an alkyl compound attached to the silica nanotube. The bioparticle can have a size from approximately 1 to 100 nm or preferably from approximately 1 to 5 nm. Enzymes can include genetically cloned enzymes.

A method for treating a patient exposed to a toxic drug includes the steps of providing a plurality of nanosized bioparticles capable of mitigating the effects of the toxic drug through at least one mechanism selected from the group consisting of partitioning the toxic drug into or onto the bioparticle and transforming the toxic drug into at least one substantially inactive metabolite, and introducing the plurality of bioparticles and then introduced into the patient. This method can also be applied to animals in the practice of veterinary medicine.

A composition for detoxification includes a plurality of nanoparticles. The nanoparticles have at least one surface adapted for toxic drug attachment. The nanoparticles are selected from the group consisting of microemulsions with nanoscale oil cores having soft surface films, hydrophobic cores having porous or soft shells and hard surfaces for selective binding of toxins. The nanoparticles can include attached enzymes for chemically degrading toxins. Preferably, the attached enzymes include genetically cloned enzymes.

DETAILED DESCRIPTION OF THE INVENTION

Bioparticles have been discovered which provide effective and generally complementary mechanisms for reducing the free concentration and biological effects of a broad range of toxins including drugs. Recent advances in particle science engineering combined with developing molecular medicine have been found to provide highly effective therapeutic strategies aimed at effectively treating a wide variety of toxic poisonings, including drug poisonings. Previously, applications for particle technology were limited by the size of available particles. For example, particles available for use had been too large to be effectively used with living organisms.

With a reduction in size of available particles to less than 100 nm, or even as small as typical molecular dimensions (1–5 nm), the invention has created bioparticles having nanoparticle sizes which are small enough to effectively interact with living organisms. It is noted that molecules may be less than 1 nm in diameter or larger than 5 nm in diameter. For example, proteins which are polymers or macromolecules can be 5 nm or larger in diameter. As used herein, the term nanoparticles refer to particles having sizes less than approximately 100 nm. These bioparticles can act to bind with targeted drugs and other toxic substances and/or to quickly degrade these drugs and toxins into largely inactive reaction products. The invention can have valuable applications for a wide variety of uses such as drug detoxification (e.g., drug overdose), military (e.g., toxic warfare agents), industrial (e.g., manufacturing processes), environmental (chemical spill clean up), as well as many other purposes.

Drug poisonings may be treated by bioparticles which can use any or all of the following mechanisms:

1) partitioning a targeted drug onto the bioparticles by exploiting differences in physicochemical properties and/or using molecular templating to adsorb the drug onto functionalized surfaces of bioparticles;
2) biotransforming a targeted drug into an inactive metabolite(s). For example, an enzyme, such as a human purified and genetically cloned high activity enzyme, may be incorporated into a bioparticle to provide biotransformation effects on a targeted drug or toxin, or
3) preferably, providing a bioparticle which combines both approaches (1) and (2).

These above methods are not limited to oral or intravenous use, but could also be employed to remove toxins from biological surfaces such as skin or non-biological surfaces such as metal, wood or plastic. Moreover, the above methods can be used to detoxify a broad range of toxins.

The invention allows the synthesis of bioparticles that can directly reduce the free drug concentration in the blood, either by exclusively partitioning it inside the bioparticle, or more preferably, by partitioning and biotransforming the drug into an inactive metabolite within the bioparticle and ultimately promoting excretion from the body. With this approach, the principles of lipid partitioning and/or adsorption (via molecular templating) may act in a highly synergistic manner with those of biotransformation to provide drug detoxification systems with complementary detoxification mechanisms to provide added effectiveness. Thus, by providing a very high local concentration of toxic drug (substrate), partitioning and/or adsorption can dramatically increase the rate of enzymatic degradation depending upon the KM of the enzyme and its enzymatic efficiency in the bioparticle.

Nanoparticles (such as those shown in FIG. 1) have been created for treating a broad range of toxins. For example, "soft particles" such as microemulsions with nanoscale oil cores and "soft/hard" particles with hydrophobic cores for lipophilic drugs and various shells each permit relatively selective drug penetration. "Templated particles" allow for toxins to be selectively fitted into pores in their surface generally with 1 or 2 point binding of the toxin to the nanoparticle. The above nanoparticle types can preferably also include an attached enzyme for even more rapid degradation of the target drug and/or toxin.

Soft/hard particles are ones consisting of a core composed of a liquid or a (softer) polymeric organic material surrounded by or encapsulated in a shell composed of an inorganic or (harder) polymeric organic material. The example of a liquid encapsulated in a shell of metal oxide or metal carbonate can be prepared by making a solution of the metal oxide precursor in an oil and exposing droplets of the solution to water or carbonate ion, respectively. This could be accomplished in aerosol or microemulsion apparatus. The example of a liquid encapsulated in a shell of organic polymer can be prepared by making a microemulsion stabilized by surfactant having reactive vinyl functionality, followed by initiating polymerization of the surfactant molecules around the surface of individual oil droplets in the system. The example of a (soft) polymeric organic core encapsulated in a (hard) polymeric shell can be prepared by dispersing a polymer gel in a solution of organic monomer precursor to a highly crosslinked or crystalline polymer, followed by initiation of polymerization of the dissolved monomer.

Templated particles are ones consisting of material, either as the core or shell component, that incorporates molecularly-sized and shaped pores into its structure. These materials can be prepared by including in the synthesis mixture suitably derivatized molecules or mimics (the templates) of the chemicals (in this application the toxins) of interest to be captured by the bioparticles. After the particles are formed and collected, the templating species are removed from the particles by dialysis or pyrolysis, leaving the desired pores as selective sites in which toxic molecules to be removed can be trapped. Examples are various metal oxides or solid organic polymers that have pores templated for neural amines, aromatic compounds or terpenes.

A shell containing pores can provide significant improve the effectiveness of nanoparticle-mediated drug detoxification. There are a number of potential design benefits of encapsulating either a hydrophilic or a hydrophobic environment with a solid shell containing nanopores. First, it could act to stabilize a nanoemulsion injected into the blood to prevent a dilutional effect on emulsion function. Second, it could act as a highly selective molecular filter by allowing only molecules of certain physical dimensions access to the bioparticle interior. Therefore, bioparticles could be targeted against at toxic molecules with molecular weights (MWs) at or below the selected cutoff points of molecular size. Third, by "trapping" locally high concentrations of coenzymes and cofactors important to CYP activity such as oxidoreductase (MW=75,000) and cytochrome b5 (MW=17,500) within the bioparticle interior and preventing their escape, a bioparticle with a shell incorporating nanopores would potentially enhance (or at least help preserve) optimal P450 enzymatic activity.

The reconstitution of P450 enzymes, especially the CYP 3A4 fraction, may be technically challenging with regards to preserving its catalytic activity, especially in blood. Inclusion of a shell can greatly aid this process. Fourth, a bioparticle shell with nanopores could prevent proteolytic degradation of CYP fractions while in the blood (i.e., armor the enzymes). It will allow ingress of smaller sized toxic drug molecules and easy egress of more water-soluble metabolites, but exclude those molecules greater than the pore size cutoff. In contrast, CYP fractions incorporated into soft bioparticles may not only be susceptible to degradation in blood, but their local concentrations of cofactors and coenzymes may not be preserved (see the second point given above). Fifth, a solid shell with nanopores could be designed to provide a biodegradable platform where the functional activity of the bioparticle is determined by the blood half-life of biodegradable shell. That is, once the job of biotransformation is complete, the biodegradable particle can slowly disintegrate and releases the CYP fractions into the blood where they are degraded. Sixth, design of the shell and its surface characteristics (e.g., ionicity, lipophilicity) may be critical to prevent (or minimize) uptake into RBCs or the reticuloendothelial system (RES), or eliminate the risk of hemolysis. The goal of bioparticle design is to keep the bioparticles within the vascular compartment. Seventh, if the shell of the nanobioparticle is sized small enough to be directly excreted via the kidney, it may be possible to directly sequester a highly lipophilic drug within the bioparticle via partitioning and/or adsorption, or to attach it to even smaller sized nanoparticles by adsorption onto its surface.

In a manner similar to what is observed clinically when the Fab antibody Digibind® is used to treat digoxin toxicity, if the size of the "nanoparticulobody" (a bioparticle acting functionally like an antibody) is less than a 50,000–60,000 MW molecule, it may be directly excreted from the body by the kidneys, particularly if its surface has a neutral or positive charge. Using molecular templating, highly selective adsorption of various molecules (and members among their chemical class) can be achieved. In this scenario, the P450 element of the bioparticle would not be needed. In essence, the nanoparticle is accomplishing Phase I and II biotransformation without the actual need for enzyme modification. That is, it renders the toxic drug molecule more polar by complexing it to a nanoparticle, which in turn allows excretion from the body. This type of adsorption would be highly selective and would most likely be applicable only to those molecules (or class of drugs sharing a common chemical moiety) it was originally designed for. In contrast, if a lipid partitioning system could be incorporated into a bioparticle, while keeping its size less than 50–60 kDa, it would be useful for most lipophilic drugs.

One approach for preparing such nanoparticles entails using the template-synthesis method. In this method, the pores in a microporous membrane or other solid are used as templates to prepare the nanoparticle. The membranes employed contain cylindrical pores with monodisperse diameters. The pore diameter can be controlled at will over a range from less than 1 nm to as large as tens of micrometers. A correspondingly large range of nanoparticle sizes can be prepared. The template method is very versatile. It has been used to prepare nanoparticles composed of metals, semiconductors, other inorganic materials, carbons, etc. Nearly any method used to prepare bulk materials can be adapted to allow for synthesis of nanoparticles within the pores of a microporous template membrane. Significantly, a hollow tubular nanostructures can be obtained.

Membranes that have been used to prepare nanoparticles via the template method are shown in FIG. 3. These are microporous aluminas prepared electrochemically from aluminum metal. The upper set of micrographs shows an in-house prepared membrane of this type. In this case the pores are approximately 60 nm in diameter. The lower micrograph in FIG. 3 shows a commercially-available membrane of this type. In this case the pores are 200 nm in diameter. These micrographs illustrate the important point discussed above that the pore diameter in such membranes (and correspondingly the diameter of the nanoparticle obtained) can be controlled at will. For these microporous alumina template membranes, the pore diameter is varied by varying the potential used during the electrochemical formation of the membrane.

Toxins can be adsorbed onto specialized nanoparticles to achieve drug detoxification. Nanoemulsions have been synthesized for acutely reducing the free concentration of potentially toxic molecules. FIG. 2 shows the effect of Pluronic® L-44 Micelles and microemulsions in reducing the concentration of the drug amitriptyline. A micelle may be defined as a colloidal aggregate of amphipathic (surfactant) molecules, which occurs at a well-defined concentration known as the critical micelle concentration. The typical number of aggregated molecules in a micelle (aggregation number) is from approximately 50 to 100.

Poloxamer, or Pluronic® gels are made from selected forms of polyoxyethylene-polyoxypropylene copolymers in concentrations ranging from 15 to 50 weight %. Poloxamers generally are white, waxy, free-flowing granules that are practically odorless and tasteless. Aqueous solutions of poloxamers are stable in the presence of acids, alkalis and metal ions. Commonly used poloxamers include the 124 (L-44 grade) used above as well as 188 (F-68 grade), 237 (F-87 grade), 338 (F-108 grade) and 407 (F-127 grade) types, which are freely soluble in water. The trade name "Pluronic®" is used in the US by BASF Corp., of Mount Olive, New Jersey, for pharmaceutical and industrial grade poloxamers.

In the example shown in FIG. 2, a nanoemulsion was produced using Pluronic® L-44 (micelles) with or without addition of ethylbutyrate ester. Ethylbutyrate ester was added at a low (ME-I) and high (ME-II) concentration. As seen in FIG. 2, the emulsion effectively sequestered significant quantities of amitriptyline, a tricyclic antidepressant agent with potential cardiotoxic effects, when compared to the saline control shown. The system labeled "Micelles" did not possess the oil core of ethylbutyrate ester which was possessed by both ME-1 and ME-II. By comparing the Micelles system to ME-1 and ME-2, it can be seen that the oil core significantly increased the amount of amitripyline adsorbed, the higher oil concentration (ME-II) adsorbing significantly more amitripyline than the lower oil concentration (ME-I). Drugs that may be amenable to this type of detoxification are not limited to tricyclic antidepressant agents such as amitriptyline, but may include drugs and toxins from all drug classes that have an affinity for, tend to combine with, or are capable of dissolving in lipids (lipophilic drugs).

Many types of oils, surfactants, and cosurfactants may be used to produce bioparticles based on nanoemulsion technology. The bioparticle composition can be varied depending on the goal of the therapy and the specific properties of the target toxin. For example, a particle system prepared for intravenous use would, be preferably varied in composition compared to a similar system prepared for skin or metal decontamination.

Another type of bioparticle that can be used to detoxify drugs can be prepared using the template-synthesis method. Template-synthesized nanoparticles can be either hollow nanotubules or solid nanoparticles and they can remove the toxic substance by either adsorption on their surfaces or extraction into the hollow part of the nanotubule. Such template-synthesized nanoparticles can be composed of a wide variety of materials including metals, polymers, semiconductors, other inorganic materials, carbons, etc. The size of these nanoparticles (both the diameter and the length) can be controlled at will from the nm regime to the micrometer regime.

One embodiment of this technology is to use the template method to prepare hollow cylindrical silica nanoparticles. These nanoparticles are preferably prepared by using sol-gel template synthesis of silica within the pores of a microporous alumina template membrane. The silica tubules in this case were prepared using tetraethylorthosilicate as the starting material; however, other precursors are available for preparing silica via the sol-gel method. Sol-gel silica nanotubules of this type have been prepared in the pores of various microporous alumina template of the type shown in FIG. 3. It has been shown that both the inside and outside diameters and the length of the silica nanostructures can be controlled by varying the diameter of the pores and the thickness of the template used.

The tubular silica nanostructures prepared in this way can be derivatized both on their outside and inside surfaces with chemical and/or biochemical reagents. One approach for doing this is to use well-known silane chemistry. Hundreds of silanes are available commercially, so this is a very versatile route for chemically and biochemically derivatizing these silica nanostructures. This is important because such derivatization allows these nanotubules to extract or adsorb specific chemical reagents and allows them to catalyze specific biochemical reactions. In addition because the inside and outside of the tubules can be derivatized with different reagents, the inside and outside chemistry/biochemistry can be different. This is important because, for example, it might be desirable to have the interior of the nanotubules hydrophobic so that they will extract specific molecules but the outside hydrophilic so that the nanotubules can be dispersed in an aqueous-based medium (e.g. blood).

Two embodiments of this concept are discussed herein. The first embodiment derivatizes the inside surfaces of the silica nanocylinders with a hydrophobic 18 carbon alkyl silane. In this case the outside surface is left underivatized so that the outside surface retains the hydrophilic character of silica. The second case entails derivatizing both the inside and outside surfaces with trimethoxybutyl aldehyde to introduce the aldehyde functionality to the surfaces. This aldehyde functionality can then be reacted with terminal amino sites on a protein molecule to covalently attach the protein to the nanotubules. Attachment of the protein glucose oxidase (GOD) can be performed in this way. Many other proteins have been attached using this general method. Accordingly, it is a versatile way to attach proteins to the surfaces of these nanotubules.

Scanning electron micrographs of an alumina template membrane having a plurality of open pores which can be filled with silica nanotubes are shown in FIGS. 3(a)–3(c). FIG. 3(a) shows a surface image of an alumina template membrane demonstrating a high packing density of pores, the pores having diameters of approximately 60 nm. FIG. 3(b) shows a cross sectional image of the template membrane shown in FIG. 3(a) while FIG. 3(c) shows a perspective view of the template membrane. Although 60 nm nominal pore diameters are shown, pore diameters of the template membrane can be readily controlled.

In an embodiment of the invention, a long chain alkyl carbon (such as $C_{18}$) is added to silica nanotubes positioned within a template membrane for the purpose of adsorbing a target molecule. It is noted that the field of protein and enzyme attachment to particles, otherwise referred to pro-lifically in the literature as "enzyme immobilization", is a mature science, and that the methodologies described in this portion of the application are similar to ones described earlier but that the selection of which enzymes used and the overall particle composition is unique.

The 18-carbon alkyl ($C_{18}$) silane was chosen because this renders the insides of the nanotubules hydrophobic. The nanotubules with the $C_{18}$ groups inside can then be used to extract hydrophobic molecules from a contacting solution phase. Again, in this case the outsides of the nanotubules remain hydrophilic silica and this allows these tubules to be dispersed into solutions containing polar solvents. The most obvious example is water, but the same principle applies for other polar solvents. Obviously, the outside could also be derivatized with the hydrophobic silane and such tubules could then be dispersed into solutions containing nonpolar solvents. Other alkyl silanes could be used to tune the extraction selectivity of the derivatized nanotubules. Examples include using shorter chain (e.g. $C_8$) alkyl silanes to make the tubules less hydrophobic on the inside, using aromatic silanes, using silanes with specific chemical functionalities (e.g., acidic or basic), etc.

The hydrophobic $C_{18}$ silane-containing tubules were used to extract a hydrophobic target molecule (7,8-benzoqunoline or BQ) from a dilute aqueous solution. Extraction was accomplished in two ways. In the first method the hydrophobic nanotubules were left embedded within the pores of the template membrane, and a piece of the membrane was simply immersed into and then removed from the solution of the target molecule. Removing the membrane also accomplished the removal of the target molecule BQ sequestered inside. In the second method, the nanotubules were liberated from the template membrane, by dissolving the membrane in phosphoric acid solution. The liberated tubules were then collected by filtration. The tubules were then dispersed into a solution of the target molecule. The solution was then filtered to remove the tubules as well as the target molecule BQ sequestered inside.

Figure 4:
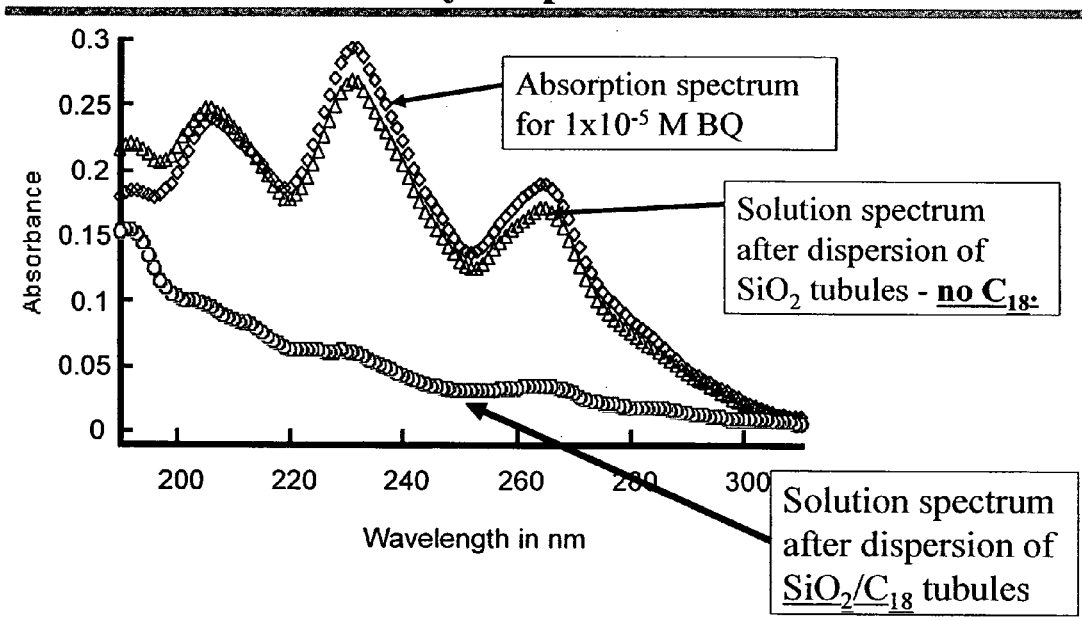

FIG. 4 shows an example of the second method, dispersion of the liberated nanotubules. This figure shows first the UV absorption spectrum of a solution that was $1\times10^{-5}$ M 7,8 benzoquinoline solution (BQ). To this solution was first added silica nanotubules that did not contain the hydrophobic $C_{18}$ silane inside. (10 mg of tubules added per 100 mL of solution.) The solution was then filtered to remove these tubules and the solution spectrum was remeasured. Note that there is essentially no change in the BQ absorbance. This experiment showed that silica tubules that were hydrophilic on the inside did not extract the hydrophobic BQ.

Figure 5:
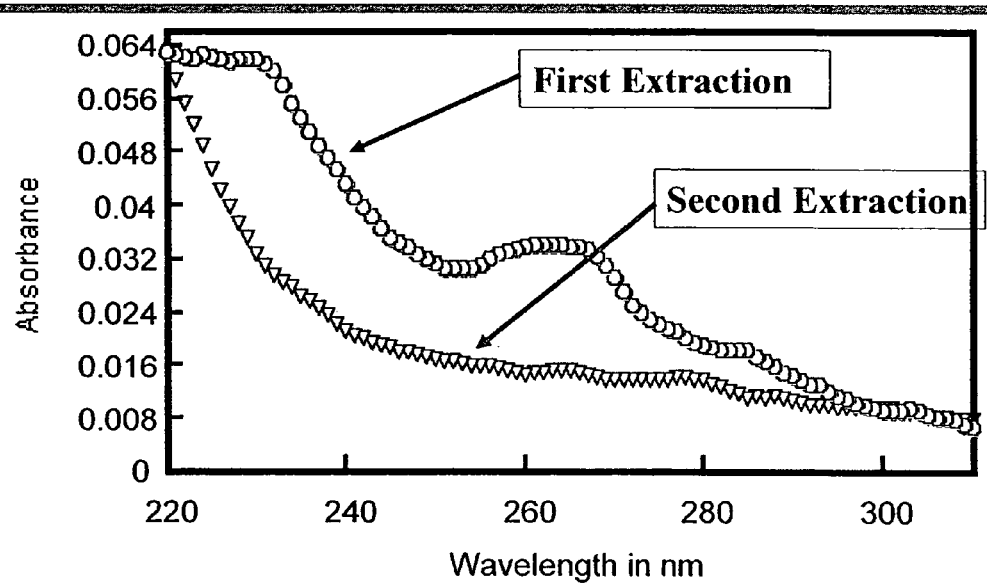

An identical quantity of the $C_{18}$ derivatized tubules was then added to the solution. The solution was then filtered to remove the tubules and the spectrum was remeasured. As indicated by the lower absorbance, these tubules extracted 82% of the BQ from the solution. FIG. 5 shows analogous data after addition of a second 10 mg of tubules per 100 mL of solution. After the second extraction 92% of the BQ was removed from the solution.

In another embodiment of the invention, reactive molecules such as enzymes can be incorporated into nanoparticles to improve the drug detoxification ability of the nanoparticles. Although enzymes are described herein, incorporation of any molecule capable of generating a chemical reaction or aiding in the rate of a chemical reaction with a target molecule can also be incorporated in nanoparticles to produce enhanced detoxification results. This approach detoxifies substances and surfaces by using nanoparticles as a platform to incorporate molecules such as enzymes for catalyzing the conversion of toxic substances into inactive substances (or for generating chemical reactions with toxic substances).

Protein (i.e., enzyme) attachment to $SiO_2$ nanotubules was achieved using 2 steps. A tubule wall was functionalized with an aldehyde-terminated silane. A protein was then coupled to the aldehyde through primary amino sites on the protein. The enzyme used, glucose oxidase (GOD), was the first protein tested. GOD effectively catalyzes the oxidation of glucose to glucono-1,5-lactone. In the presence of glucono-1,5-lactone, electrons shuttle to $O_2$, creating hydrogen peroxide. In the presence of peroxidase (POD), hydrogen peroxide oxidizes o-dianisidine from a colorless to red form, which then can be assayed by monitoring its absorbance (See FIG. 6).

Figure 6:
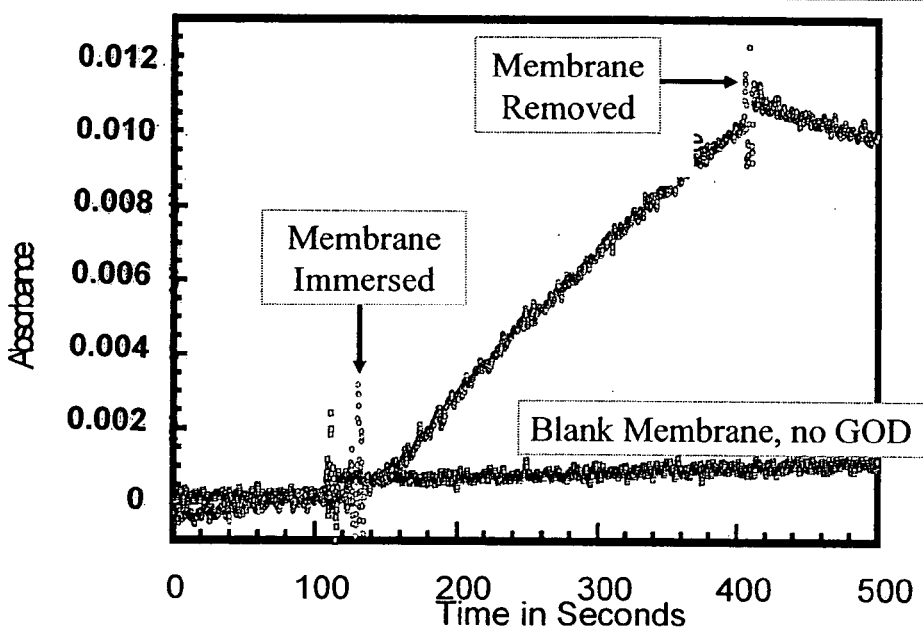

For preliminary experiments performed, an intact alumina template membrane with the $SiO_2$/GOD nanotubules in the pores was utilized. The absorbance of a solution of glucose, o-dianisidine and POD immersed in a "blank membrane" (without nanotube incorporation of GOD) was determined to establish a baseline absorbance. $Al_2O_3$/$SiO_2$/GOD membranes were then immersed into the glucose solution. The time dependent changes in the absorbance (concentration) of glucose (assayed indirectly via oxidation of o-dianisidine) were determined. The results are depicted in FIG. 6. Based on the absorbance spectra shown, it is apparent that GOD incorporated into pores of the nanotubules converted much of the glucose in the solution to glucono-1,5-lactone upon immersion of the membrane (at approximately 140 seconds). As shown in FIG. 6, at approximately 400 seconds the membrane was removed from the solution. No further oxidation of glucose is observed because in removing the membrane the GOD incorporated inside is removed.

The nanotubes are important because they are new morphologies of particulate material. They are also important, being newly available, for evaluation and use in biomedical applications either by themselves or modified as described in this application. However, the nanotube is not the only shape carrier/core particle that can be derivatized as is described in this application. Many other shapes are useful, such as derivatized polyhedral-shaped porous (templated or not) nanoparticles.

Based on this observation, it was concluded that enzymes incorporated into nanoparticles can be used to degrade drugs. The linkage of enzymes to the inner surface of pores, can be achieved without losing the enzyme's reactivity. Although nanotubes having inner cavities for enzyme attachment was used, any shaped particle, whether tubular or not, having pores adapted for this purpose can have enzymes inside the pores. Thus, any nanoparticles having pores, whether the pores are tubular or any other shape may be used with the invention.

An identical approach (i.e., linking a cytochrome P-450 (CYP) enzyme system) to the inner surface of a nanoparticle) can also be used to efficiently reduce the free concentration of lipophilic agents in human plasma and blood by a biotransformation dominated mechanism.

Analogous experiments have been done with nanotubules that were liberated from the template membrane, and substantially identical results were obtained. In this case the GOD was on both the inner and outer surfaces of the membrane. This is an advantage of the hollow nanotubule approach. Having available inner and outer surfaces increases the surface area available for biocatalysis. As before, it might also be advantageous to separately derivatize the inner and outer surfaces. For example, the inner surface could be derivatized with a specific dye and the outer surface could be derivatized with a specific enzyme or other protein. In a second set of tubules, a second specific dye could be attached to the inside and a second specific protein to the outside. This could be continued for n tubules that contain specific dyes and specific proteins on the insides and outsides. The dye could then be used to identify the tubules. For example, green tubules could contain protein #1, blue tubules could contain protein #2, etc. In this way, in a mixture of tubules one could identify which tubules are catalyzing which biochemical process.

Hollow and solid nanoparticles can also be used for removal of lipophilic toxins. For example, nanoparticles, whether hollow or solid, having substantially polyhedral or spherical morphologies can be used for this purpose. Studies were performed to establish whether the benzene ring moiety of the prototypical amide local anesthetic, bupivacaine, possessed sufficient electron enrichment to enable TT—TT electron bonding to an electron deficient molecular moiety attached to a solid nanoparticle. Specifically, when a mimic of bupivacaine was mixed with the dinitrobenzamide moiety, a number of changes in spectral values occurred. Specifically, the UV-VIS diffuse shoulder from 280–320 nm moved to a diffuse shoulder from 340–400 nm.

Complexation of the pi—pi type between bupivacaine and its mimics, and several electron deficient aromatics, including a dinitrobenzamide (designed for convenient subsequent attachment to nanoparticles), has been proven using proton NMR spectrometry. Tables 1 and 2 show the chemical shift values observed for test systems relevant to this application.

TABLE 1

Values of Shift for Donor-Trinitrobenzene
Complexes in Chloroform-d

| Donor | Shift (ppm, for acceptor) | Direction |
| --- | --- | --- |
| 2,6-Dimethylaniline | 0.2995 | Upfield |
| 2,4-Dimethylaniline | 0.3086 | Upfield |
| 3,5-Dimethylaniline | 0.2647 | Upfield |
| 3,4-Dimethoxytoluene | 0.2730, 0.1868b | Upfield | notes: a [donor:acceptor] = 60:1 b at concentration in literature, lit. Value = 0.1830

TABLE 2

Values of Shift for Donor-N-Methyl-3,5-dinitrobenzamide
Complexes in Chloroform-d

| Donor | Shift (ppm, acceptor) | Direction |
| --- | --- | --- |
| 2,6-Dimethylaniline | Triplet 0.0874 | Upfield |
|  | Doublet 0.0779 | Upfield |
| 2,6-Dimethylacetanilide | Triplet 0.0156b, 0.1584 | Upfield |
|  | Doublet 0.00775b, 0.0055 | Downfield, Upfield |

TABLE 2-continued

Values of Shift for Donor-N-Methyl-3,5-dinitrobenzamide
Complexes in Chloroform-d

| Donor | Shift (ppm, acceptor) | Direction |
| --- | --- | --- |
| Bupivacaine (salt)c | Triplet 0.0891 | Upfield |
|  | Doublet 0.0275 | Upfield | notes: a [Donor:Acceptor] = 60:1, except case b where [D:A] = 1:1; c Studied in 50:50 D20:CD3CN This data is consistent with the ranges published (Dust, 1992) for other TT complexed electron deficient and electron rich benzene rings. Thus, the dinitrobenzamide moiety can be attached to carrier nanoparticles during synthesis for use treating local anesthetic detoxification primarily by TT—TT complexation which can take place on solid or soft/hard nanoparticles, and with or without two-point binding or templated cores or shells.

Figure 7:
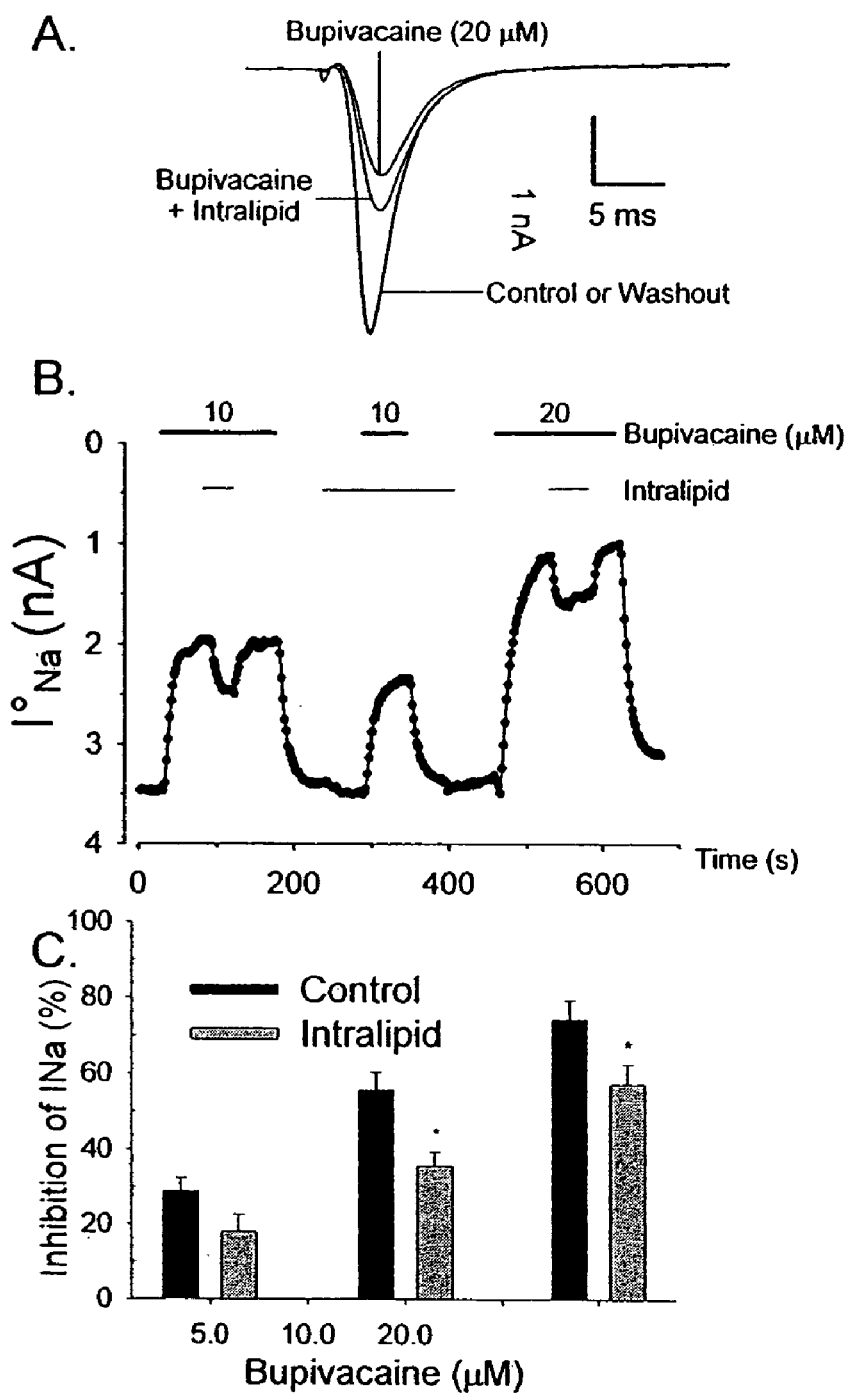
Figure 8:
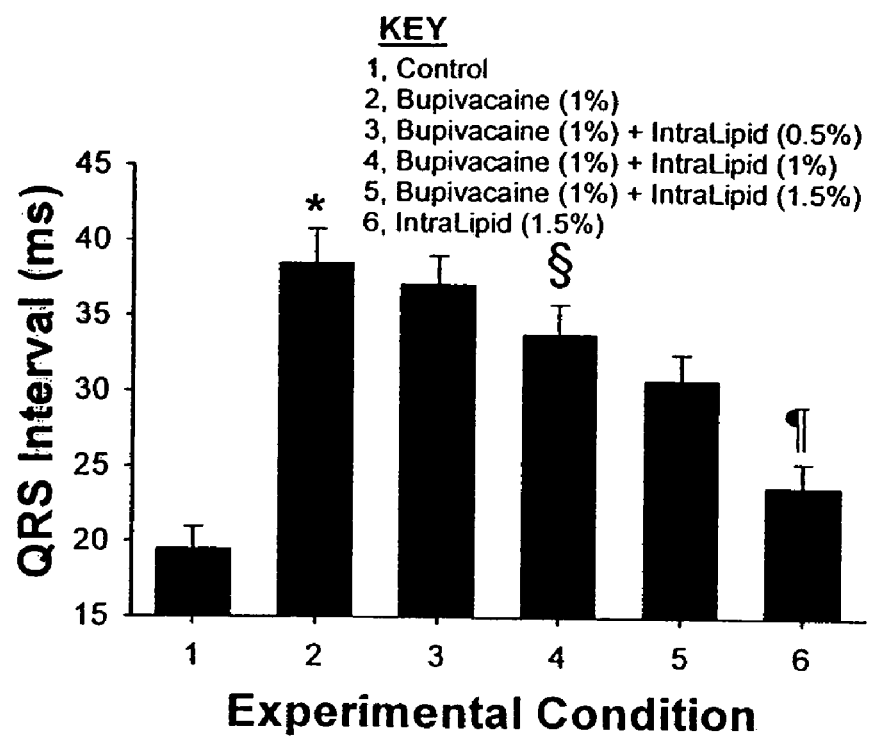
Figure 9:
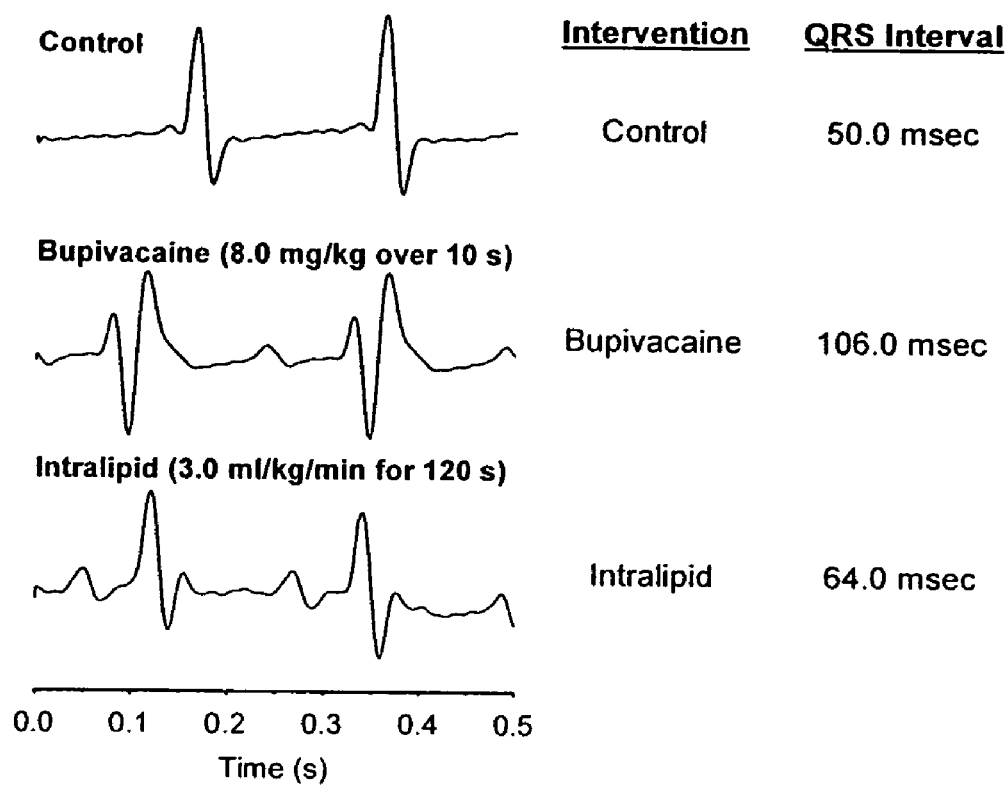

Further experiments were performed to determine the effectiveness of various emulsions to reduce the free concentration and toxic effects of other drugs. As shown in FIGS. 7–9, the cardiotoxic effects of bupivacaine, a local anesthetic, were significantly reduced using a macroemulsion of Intralipid.

FIG. 7 shows a macroemulsion of Intralipid. Intralipid attenuates bupivacaine-induced sodium current ($I_{ns}$) in guinea pig ventricular myocytes. Panel A shows examples of current traces in response to depolarization to −20 mV from a holding potential of −100 mV during interventions shown near each records. Panel B shows the change in current peaking as a function of time. Horizontal bars above panel B denote the duration of drug administration. Panel C summarizes the effect of bupivacaine (5, 10 and 20 $\mu$M) and Intralipid (1.5%) on $I_{ns}$. All data was normalized to a control current. Bars represent the mean±SEM of 5–7 myocytes.

FIG. 8 shows concentration-dependent in vitro attenuation of bupivacaine (1 $\mu$M). Bupivacaine induces QRS prolongation in guinea pig isolated hearts, paced at 200 beats per minute (BPM) as shown in FIG. 8. FIG. 8 shows the mean ±SEM of 4 experiments (P<0.05). As shown in FIG. 8, increasing Intralipid concentations reduce QRS prolongation caused by bupivacaine 1%.

FIG. 9 shows the attenuation of in-vivo cardiotoxic effects of bupivacaine in isofluanc-anesthetized rates. Specifically, the effect of an IV bolus of bupivacaine (8 mg/kg over 10 sec) on the QRS interval is shown. Compared to time matched controls, Intralipid (3 ml/kg/min over 2 min) more rapidly attenuated bupivacaine induced prolongation of the QRS interval. Two additional experiments were also carried out, both yielding similar results.

Therefore, compared to available methods, bioparticles which may be produced using the invention have numerous advantages over current methods for treating drug toxicity. Advantages from the invention are enhanced through use of complementary approaches including lipid partitioning, adsorption and xenobiotic biotransformation.

Bioparticles using lipid partitioning and/or drug biotransformation produced using the invention not only scavenge most toxic drugs that are more lipophilic (active drug state normally, but also offer broader substrate usage. For example, various soft bioparticles can effectively reduce the free blood concentration of all virtually lipophilic drugs. Moreover, appropriately chosen enzymes incorporated into bioparticles can further improve the bioparticle's therapeutic performance and applicability by adding metabolization effects applicable to a broad range of drugs. If desired, the feature of chemical selectivity inherent in immunotoxicotherapy can be incorporated into bioparticles by using the processes of molecular templating and/or adsorption onto functionalized surfaces.

Using bioparticles, large lipid-water partition coefficients for highly lipid soluble substances such as amiodarone indicate that the free concentration of this antiarrhythmic agent can be effectively reduced by using a concentration of soft bioparticles in the bloodstream that should not be detrimental to cell function (approximately 1.5% maximum). A bioparticle having a large lipid-water partition coefficient (e.g. 10,000), where the lipid component of the bioparticle is either liquid solid core, or lipophilic molecular entities attached to the surface of an inorganic core can bind a large fraction of highly lipophilic drugs. Thus, a drug's free blood concentration can be effectively reduced in a small volume of soft bioparticles.

In a preferred embodiment of the invention, bioparticles containing P450 cytochrome components such as a CYP 3A4 fraction are used to not only offer broad substrate detoxification, but also to produce rapid elimination of toxins from the blood. CYP3A4 and CYP2D6 hepatic microsomal fractions of the P450 system can biotransform approximately 55% and 25%, respectively, of virtually all xenobiotics [Benet L Z, Kroetz D L and Sheiner L B, Pharmacokinetics in Goodman and Gilman's, Pharmacological Basis of Therapeutics (1996) eds Hardman J G and Limbird L E, 9th Edition, McGraw Hill, pp 3–27.] Cytochrome results in an enhanced drug elimination rate by either increasing the quantity or quality of enzyme (e.g., selecting high activity enzyme systems using genetic polymorphisms or molecular cloning) and/or optimizing the environment of the enzyme (substrate concentration, cofactor levels, hydrophilicity for optimal enzyme functioning).

Bioparticles can provide partitioning and a biotransformation to take advantage of the potential synergistic actions which can result from initially partitioning a drug at high local concentrations in an environment containing high concentrations of an enzyme. This synergy can dramatically increase the efficiency of the substrate degradation if the toxic drug concentration occurs well below the KM value.

For example, partitioning a toxic drug from the bloodstream into the lipid environment of a bioparticle containing a genetically engineered P450 enzyme designed for super high efficiency (e.g., supersomes) should not only effectively and promptly reduce the free blood concentration of xenobiotics in the blood but also concentrate the toxic drug in an area adjacent to the active enzyme. This can promote extremely efficient catalysis and degradation of target molecules.

The beneficial effects of bioparticles formed using the invention are expected to be greatly enhanced by concentrating a large enzyme mass, such as genetically engineering P450 fractions selected for super high activity within the biocompatible particle. Preferably, the bioparticle should have a large internal surface area whose efficiency of catalyzing its substrate to its metabolite is marked augmented by the concentrating effect of the soft bioparticle component (e.g., exposes the enzyme to a high concentration of its substrate). In addition to its substrate concentrating effect, another advantage gained by incorporating a lipid matrix within the bioparticle is that this structure may dramatically increase the intrinsic biocatalytic efficiency of an enzyme. Salt-immobilized hydrolytic and co-factor requiring enzymes (lyophilizates of enzyme in a salt matrix) in organic solvents have been shown to have 100–3000 times more activity than that observed in aqueous mediums (U.S. Pat. No. 5,449,613 to Dordick, et al.). This technology applied to CYP fractions located within bioparticles can produce extremely efficient biocatalytical tools for drug detoxification, particularly when preferred high efficiently molecular cloned supersomes are used.

Numerous products can be produced from the invention including those composed of multiple types of nanoparticles for in-vivo detoxification of drugs and toxins from humans or animals. For example, nanoparticles can be synthesized for attenuating acute cardiotoxic effects of tricyclic antidepressant drugs (e.g., amitriptyline). However, the invention is not limited only to tricyclic anti-depressants, but encompasses all drug classes that may cause toxicity. In addition, biological toxins (e.g., snake and insect envenomation) may also be detoxified using the invention. This can ensure human and animal safety and welfare. Furthermore, endogenous toxins produced during organ dysfunction or failure (e.g., hepatic or renal failure) may also be removable using the invention to create "circulating hepatocytes" or "circulation nephons."

Another potential product which can be produced from the invention is a product for detoxification of poison warfare agents that are used for military purposes (e.g., nerve gas). It is noted that warfare agents may be solids, liquids or gases. Warfare agents can cause massive intoxification of substances such as acetylcholine or tissue necrosis from direct toxicity (e.g., mustard gases). Rapid and simultaneous removal of both the warfare agent and molecules causing injury may prove to be effective therapy to mitigate the dangers of these weapons of mass destruction. For example, bioparticles produced using the invention could be used intravenously to reduce the concentration of both the toxin (e.g., sarin) and acetylcholine. Alternatively, the invention can be used for skin or metal decontamination for other types of toxic warfare agents such as mustard gas.

We claim:

1. A particle, comprising:

(a) a first region comprising an enzyme that transforms a toxic compound into a substantially inactive compound; and (b) a second region comprising a material that partitions said toxic compound into said second region; wherein said partitioning results in a high local concentration of said toxic compound, wherein said first region is in contact with at least a portion of said second region.

2. The particle of claim 1, wherein said material that partitions said toxic compound into said second region is hydrophobic.

3. The particle of claim 1, further comprising a surface film, wherein said material that partitions said toxic compound into said second region is an oil, wherein said surface film encapsulates said oil, and wherein said enzyme is dispersed in said oil.

4. The particle of claim 1, further comprising an inorganic or polymer shell, wherein said material that partitions said toxic compound into said second region is an oil, wherein said inorganic or polymer shell encapsulates said oil, and wherein said enzyme is dispersed in said oil.

5. The particle of claim 4, wherein said inorganic or polymer shell is porous to said toxic compound.

6. The particle of claim 4, wherein said inorganic or polymer shell contains pores.

7. The particle of claim 1, wherein said first region further comprises a hollow tube open at least at one end; wherein said hollow tube comprises an inorganic or polymer material; wherein said enzyme is attached to a surface of said tube and wherein said material that partitions said toxic compound is a hydrophobic compound attached to an inside surface of said tube.

8. The particle of claim 7, wherein said inorganic material is silica.

9. The particle of claim 7, wherein said hydrophobic compound is an alkyl compound.

10. The particle of claim 1, wherein said particle has a size from approximately 1 to 200 nm.

11. The particle of claim 10, wherein said particle has a size from approximately 1 to 5 nm.

* * * * *